(12) United States Patent
Gaca et al.

(10) Patent No.: US 6,807,977 B1
(45) Date of Patent: Oct. 26, 2004

(54) METHOD AND DEVICE FOR MONITORING THE FLOW OF OIL PERTAINING TO A DEVICE FOR THE OIL AND AIR LUBRICATION OF COMPONENTS

(75) Inventors: Hans Gaca, Offenbach/Main (DE); Goetz Spiess, Berlin (DE)

(73) Assignee: Willy Vogel Aktiengesellschaft, Berlin (DE)

( * ) Notice: Subject to any disclaimer, the term of this patent is extended or adjusted under 35 U.S.C. 154(b) by 246 days.

(21) Appl. No.: 10/129,132

(22) PCT Filed: Nov. 13, 2000

(86) PCT No.: PCT/EP00/11202

§ 371 (c)(1), (2), (4) Date: Sep. 25, 2002

(87) PCT Pub. No.: WO01/36861

PCT Pub. Date: May 25, 2001

(30) Foreign Application Priority Data

Nov. 16, 1999 (DE) .......................... 199 56 958

(51) Int. Cl.[7] ................................ E03B 1/00
(52) U.S. Cl. ........................... 137/2; 137/4; 137/487.5; 184/7.4
(58) Field of Search ............................ 137/2, 4, 487.5; 184/7.4, 108

(56) References Cited

U.S. PATENT DOCUMENTS

| 4,210,809 A | | 7/1980 | Pelavin |
| 4,346,786 A | | 8/1982 | Midgley |
| 4,519,247 A | * | 5/1985 | Horttonen .................... 73/198 |
| 4,599,888 A | | 7/1986 | Hufton et al. |
| 4,713,603 A | | 12/1987 | Thorn |
| 5,083,862 A | | 1/1992 | Rusnak |
| 5,466,946 A | | 11/1995 | Kleinschmitt et al. |
| 5,813,496 A | * | 9/1998 | Hyvonen et al. ............ 184/6.4 |

FOREIGN PATENT DOCUMENTS

| EP | 0 924 509 | 6/1999 |
| JP | 02 271197 | 11/1990 |

\* cited by examiner

*Primary Examiner*—Ramesh Krishnamurthy
(74) *Attorney, Agent, or Firm*—Oblon, Spivak, McClelland, Maier & Neustadt, P.C.

(57) ABSTRACT

A method and apparatus to automatically monitor a lubricant supply of a unit lubricated according to the principle of oil and air lubrication. The method and apparatus detect oil streaks traveling on the wall of the lubricant line by using a capacitive or opto-electronic control. The method and apparatus further utilize signals that depend on wave movements of these streaks for control purposes.

17 Claims, 1 Drawing Sheet

METHOD AND DEVICE FOR MONITORING THE FLOW OF OIL PERTAINING TO A DEVICE FOR THE OIL AND AIR LUBRICATION OF COMPONENTS

BACKGROUND

The invention refers to a method of monitoring an oil flow in a means for the oil and air lubrication of units or the bearings thereof, in which oil drops are transported by an air flow along a wall of a tube and are thereby expanded in a streak-like manner, wherein fluctuations of the oil flow are detected and a signal that corresponds to the fluctuations is output, and wherein the fluctuations of the oil flow are detected by a streak sensor, which detects a streak shape, streak size, streak frequency and/or streak sequence of the oil flow on the wall of the tube in an opto-electronic manner.

The so-called oil and air lubrication is a rational lubrication method whose use is preferred if a finely metered oil flow shall be supplied in a possibly continuous way to a friction mark. The latter is for instance the case in quickly running rolling bearings as they are used amongst others in spindles of tool machines. The monitoring of the oil flow was formerly the job of the operating personnel by direct inspection (user manual: Schmierungstechnik Zentralschmieranlagen, Willy Vogel AG, 1966, pg. 4.15).

It is clear that the above-mentioned monitoring did not only require the use of transparent pipelines but also a sufficient attention of the respective operator.

A lubricating means is known from DE 44, 39 380 A1, in which oil is released from a flowing film by air flow in small droplet particles and supplied to a lubricating point. An oil atomization is to be avoided. A dynamic measurement of the oil flow rate is possible by a light sensor of the device of DE 44 39 380 A1.

In the device of JP 02 271 197 an oil film is transported on a wall by means of an air flow and it is monitored by infrared sensors.

The object of the invention to provide a method of the type taken into consideration which enables an automatic monitoring of the lubricant supply of a bearing portion with the character of the means taking the oil-air lubrication into consideration.

This object is solved according to the invention in that fluctuations of the oil flow are detected by a streak sensor and that a signal corresponding to the fluctuations is output by the streak sensor.

The method according to the invention utilizes the wavy travel movements of the oil streaks to either influence the lubrication process preferably by detecting the frequency of the crests or hollows of a wave, or to turn off the lubricating unit in the case of an inadequate provision of lubricant or in the case of a failure of the lubricant supply.

The subject matter of the invention is moreover a device for monitoring the oil flow of a means for the oil and air lubrication of components.

The invention will now be described by means of the block diagrams shown in the enclosed drawings.

DETAILED DESCRIPTION

Figure 1:
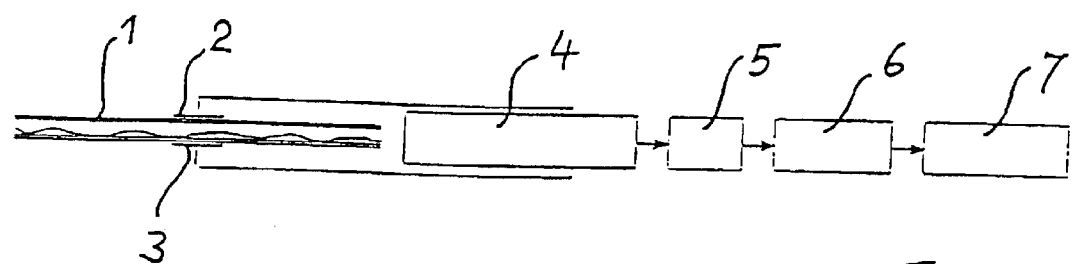
FIG. 1 is the schematic view of a monitoring device operating on a capacitive basis.

FIG. 1 shows a relatively narrow plastic tube, which in practice has a strength of approximately 4 mm, which should have a length of at least 1 m, to ensure the desired streak formation of the oil film that is not mixed with the transport air in front of the monitoring point. Two electrodes 2 and 3 partially encompassing the tube 1 adapted to the shape of the wall are arranged on opposing sides of the tube 1, said electrodes forming plates of a capacitor whose field being influenced by the sequence, shape and size of the streaks of the oil flow and whose changes in capacitance are detected by a type of electrometer 4 and are supplied via a filter 5 and a time member 6 to the switching unit 7 of a control unit, which either changes the oil quantity introduced into the tube 1 or which changes the strength of the air flow or which turns of a unit to be lubricated.

Figure 2:
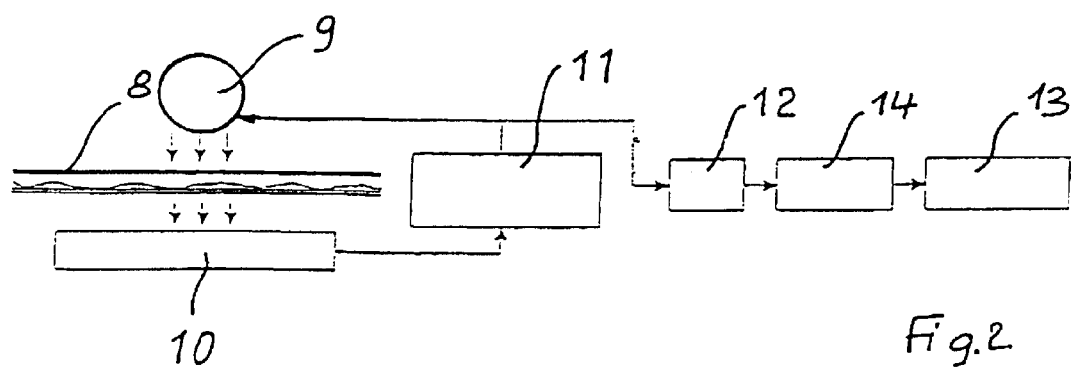
FIG. 2 is the schematic view of a monitoring device operating on an opto-electronic basis.

A second monitoring possibility is offered by the solution schematically shown in FIG. 2, in which contrary to the capacitive streak sensor according to FIG. 1 an opto-electronic streak sensor is shown.

FIG. 2 the reference numeral designates a tube made of a transparent plastic material, which has a light source 9 and a receiver 10 for the light irradiated by the light source in the area of a monitoring zone located at least 1 m away from the supply point of the oil and air flow. In order to suppress the influence of external light, the intensity of the light supplied to the receiver 10 is kept constant by the aid of a controller 11, i.e. the radiation intensity of the light source is controlled in the rhythm of the streaks in a manner that the receiver 10 is permanently biased with the same amount of light despite the fluctuating damping of the light caused by the streaks. The pulsating signals controlling the light source 9 are therefore an indicator for the existence of oil streaks.

A filter 12 provided as a band pass filter and connected downstream to the controller 11 suppresses untypical signals as they may be caused for instance in the case of changes of the sun light. The time member 14 connected upstream of the switching unit 13 fulfills the same function as the time member 5.

What is claimed is:

1. A method of monitoring an oil flow in a device for oil and air lubrication of at least one of a unit and bearings of the unit, in which oil drops are transported through an air flow along a wall of a tube and are thereby expanded in a streak-like manner, comprising:
    detecting fluctuations of the oil flow;
    outputting a signal that corresponds to the detected fluctuations,
    wherein the fluctuations of the oil flow are detected by a streak sensor, which opto-electronically detects at least one of a streak shape, a streak size, a streak frequency, and a streak sequence of the oil flow,
    wherein radiation intensity of a light source is controlled by a controller in rhythm of the streaks such that a receiver is permanently biased by a same amount of light.

2. A method as claimed in claim 1, wherein the signal output of the streak sensor is used for generating a display.

3. A method as claimed in claim 1, wherein a signal output of the streak sensor is used for varying an oil quantity introduced into the tube.

4. A method as claimed in claim 2, wherein the signal output of the streak sensor is used for varying an oil quantity introduced into the tube.

5. A method as claimed in claim 1, wherein a signal output of the streak sensor is used for varying a strength of the air flow introduced into the tube.

6. A method as claimed in claim 2, wherein the signal output of the streak sensor is used for varying a strength of the air flow introduced into the tube.

7. A method as claimed in claim 3, wherein the signal output of the streak sensor is used for varying a strength of the air flow introduced into the tube.

8. A method as claimed in claim 4, wherein the signal output of the streak sensor is used for varying a strength of the air flow introduced into the tube.

9. A method as claimed in claim 1, wherein untypical signals of the streak sensor are suppressed by a filter.

10. A method as claimed in claim 2, wherein untypical signals of the streak sensor are suppressed by a filter.

11. A method as claimed in claim 3, wherein untypical signals of the streak sensor are suppressed by a filter.

12. A method as claimed in claim 4, wherein untypical signals of the streak sensor are suppressed by a filter.

13. A method as claimed in claim 5, wherein untypical signals of the streak sensor are suppressed by a filter.

14. A method as claimed in claim 6, wherein untypical signals of the streak sensor are suppressed by a filter.

15. A method as claimed in claim 7, wherein untypical signals of the streak sensor are suppressed by a filter.

16. A method as claimed in claim 8, wherein untypical signals of the streak sensor are suppressed by a filter.

17. A device for monitoring an oil flow in a device of oil and air lubrication of at least one of a unit and bearings of the unit, comprising:

a tube that has transparent sections, through which an air flow is directed and along whose wall oil drops expanded in a streak-like manner are formed;

a sensor arranged on the tube configured to detect fluctuations of oil flow and to output a signal corresponding to the detected fluctuations of the oil flow to an evaluation unit, wherein the sensor is formed as a streak sensor through which at least one of a streak shape, a streak size, a streak frequency, and a streak sequence is detected and that comprises a receiver and a light source directed towards the receiver, arranged in an area of at least one of the transparent sections of the tube, wherein the streak sensor comprises a controller through which light intensity of a light source is configured to be controlled such that the receiver during operation can permanently be biased with a same amount of light.

* * * * *